US00PP08128P

United States Patent [19]

Trees

[11] Patent Number: Plant 8,128

[45] Date of Patent: Feb. 2, 1993

[54] VARIETY OF GERANIUM NAMED HOT PINK SATISFACTION

[75] Inventor: Scott C. Trees, Nipomo, Calif.

[73] Assignee: Geo. I. Ball, Inc., West Chicago, Ill.

[21] Appl. No.: 743,747

[22] Filed: Aug. 12, 1991

[51] Int. Cl.[5] ..... A01H 5/00

[52] U.S. Cl. ..... Plt./87.12

[58] Field of Search ..... Plt./87.12

*Primary Examiner*—James R. Feyrer

*Attorney, Agent, or Firm*—Webb, Burden, Ziesenheim & Webb

[57] ABSTRACT

A new cultivar is characterized by a rich pink color set against a medium green foliage. The growth habit is more compact and controlled when compared to the commercial variety "Cherry Blossom".

1 Drawing Sheet

BACKGROUND OF THE INVENTION

The present invention comprises a new and distinct cultivar of *Pelargonium*×*hortorum* known by the varietal name Hot Pink Satisfaction (Oglevee No. 21, P.A.S. No. 175A). The new variety was discovered in a selected breeding program in the spring hybrid trials in 1986 at PanAmerican Seed in Elburn, Ill. The new variety is a selection from the crossing of the female parent 1584A and the male parent 1194B. The new variety was first asexually reproduced by cuttings at PanAmerican Seed in Elburn, Ill. and has thereafter been asexually reproduced by cuttings at Oglevee Ltd. in Connellsville, Penna. It has also been trial and field tested at Connellsville and has been found to retain its distinctive characteristics through successive propagations.

The new variety has the semi-double flower which is pink with a white and the medium green foliage of the female parent and the background petal color of the male parent.

The new variety differs from the female parent through a smaller white eye and smaller foliage. It differs from the male parent by having semi-double flowers rather than single flowers and by having more florets per inflorescence on plants with larger medium green foliage.

The cultivar when grown in a glass greenhouse in Connellsville, Penna. using natural light and 60° F. night, 68° F. day and 71° F. vent, has a response time of six weeks from a rooted cutting to flowering in a 10 cm. pot. The response time was determined on plants grown in soilless media employing constant fertilizer 200 parts per million of nitrogen and potassium in full light. The rooted cuttings were potted on Feb. 19, 1991 and flowered on Apr. 21, 1991.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these characteristics were collected by asexual reproductions carried out by Oglevee Ltd. in Connellsville, Penna. The plant history was taken on six week plants blossomed under natural light in a greenhouse and the color readings were taken indoors under 200–220 foot candles of fluorescent cool white light. Color references are primarily to the R.H.S. Colour Chart of The Royal Horticultural Society of London.

THE PLANT

Classification:

*Botanical.*—*Pelargonium*×*hortorum.*

*Commercial.*—Zonal geranium.

Form: Compact mound form.

*Height.*—20.0 to 22.0 cm. above the media surface.

*Growth.*—Free and early flowering; basal branching.

Strength: Stands upright without artificial support.

Foliage: Stalked leaf attachment; little or no zoning present.

Leaves:

*Size.*—7.0 to 10.0 cm. across; fully expanded leaf.

*Shape.*—Reniform; cordate base.

*Margin.*—Crenate.

*Texture.*—Slightly pubescent; slightly reflective.

*Color.*—Top: Yellow/Green Group 146A. Bottom: Yellow/Green Group 146B.

*Ribs and veins.*—Palmate venation. Color: Yellow/Green Group 147C.

Petioles:

*Color.*—Yellow/Green Group 146C.

*Length.*—6.5 to 8.5 cm.

Stem:

*Color.*—Yellow/Green Group 146C.

*Internodes.*—1.0 to 2.5 cm. in length.

THE BUD

Shape: Upright, hemispherical cluster.

Size: 3.0 to 4.0 cm. across.

INFLORESCENCE

Blooming habit: Semi-double; hemispherical; slow to shatter.

Size: 10.0 to 11.5 cm. across.

Borne: Umbel; florets on pedical, pedical on peduncle; 6.0 to 7.0 cm. above foliage canopy.

Florets:

*Form.*—Flat to slightly cupped, petaloids present.

*Color.*—Top: Red/Purple Group 58C. Eye: White. Bottom: Red/Purple Group 62B.

*Petals.*—Separate; not united; margin entire; obovate; smooth; flat to slightly cupped; 5 to 9 in number.

*Size.*—3.5 to 4.0 cm. across.

*Texture and appearance.*—Smooth; appearance from a distance is a bright candy pink floret with a white eye accented with medium green foliage.

Petaloids:

*Quantity.*—2 to 4 in number.

*Shape.*—Twisted; some petal-like; some with pollen attached.

*Color.*—Top: Red/Purple Group 58C. Bottom: Red/Purple Group 62B.

Pedicel:

*Length.*—3.0 to 3.5 cm.

*Color.*—Base (peduncle end) Yellow/Green Group 146C. Tip (stipule end) Red/Purple Group 59B.

Peduncle: Arises from the node opposite the leaf petiole.

*Length.*—14.0 to 17.0 cm.

*Color.*—Yellow/Green Group 146B.

Lasting quality: During indoor pot production the large flower head has an extended blooming period. Flowers maintain freshness for up to 14 days per umbel. Similar duration to Pink Satisfaction (U.S. Plant Pat. No. 7,599) and Salmon Satisfaction (U.S. Plant Pat. No. 7,610).

Outdoor performance: Floriferous mounded habit outdoors outperformed similar colored varieties (i.e. Misty (U.S. Plant Pat. No. 7,350), Blues).

REPRODUCTIVE ORGANS

Stamens:

*Anthers.*—2.0 to 3.0 mm. in length.

*Filaments.*—7.0 to 8.0 in length; White.

*Pollen.*—Golden Brown.

Pistils:

*Number.*—One.

*Length.*—7.0 to 9.0 mm.

*Stigma.*—5-6 parted; Red-Purple.

*Style.*—2.0 to 3.0 mm. in length.

Ovaries: Superior; pale green; pubescent; 5.0 to 6.0 mm. in length.

Fruit: None observed.

GENERAL CHARACTERISTICS

This new variety adds another beautiful color to the current 'Satisfaction' Geranium series as well as the entire Geranium market and is best compared to "Cherry Blossom" (unpatented). The clean rich pink color of Hot Pink Satisfaction is a great improvement over "Cherry Blossom" which has much paler flowers. The growth habit as well is much more compact and controlled than "Cherry Blossom".

I claim:

1. A new and distinct variety of Geranium plant, substantially as shown and described.

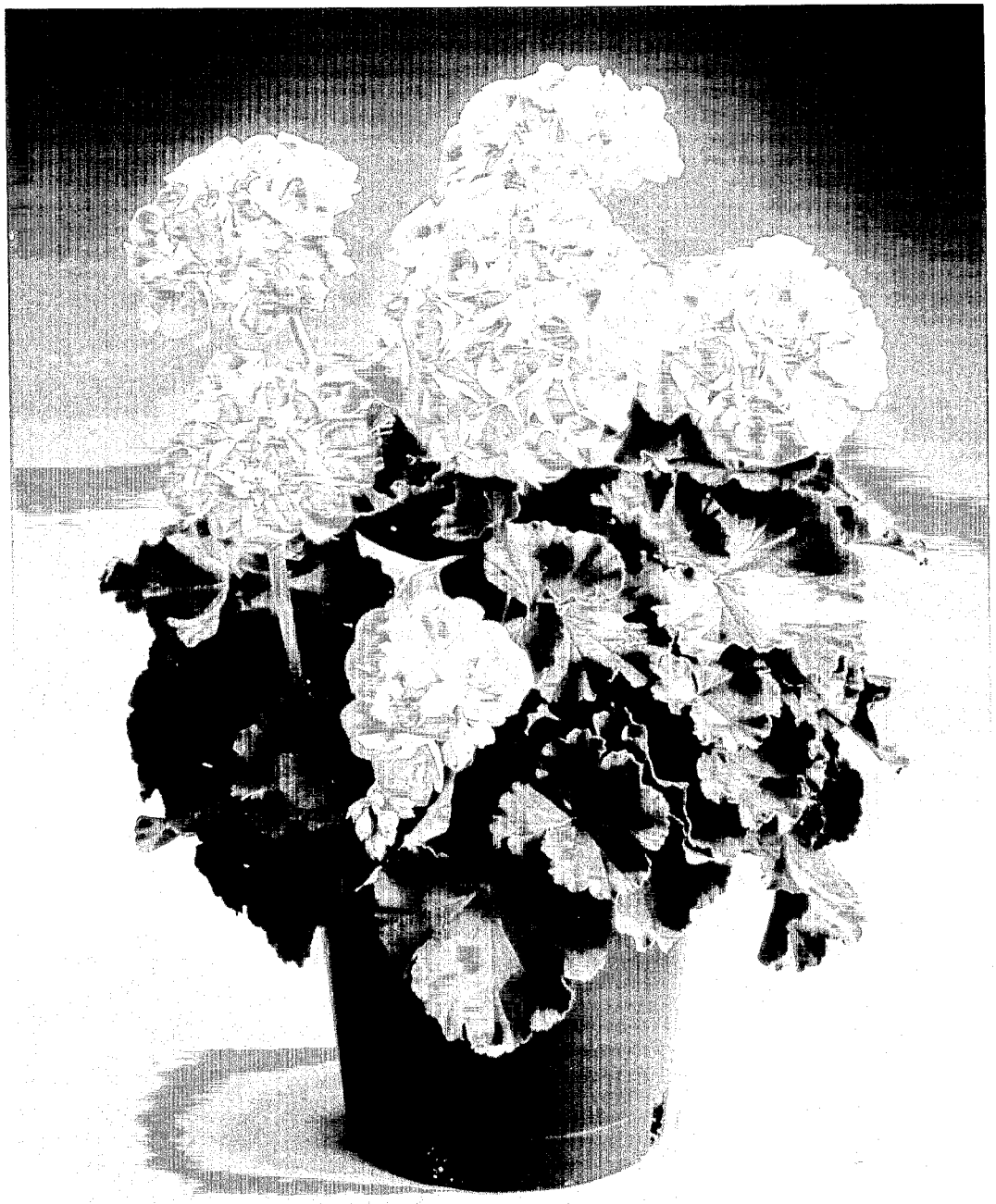

* * * * *